(12) United States Patent
Fruchey et al.

(10) Patent No.: US 8,742,060 B2
(45) Date of Patent: Jun. 3, 2014

(54) PROCESSES FOR PRODUCING HEXAMETHYLENEDIAMINE (HMD), ADIPONITRILE (ADN), ADIPAMIDE (ADM) AND DERIVATIVES THEREOF

(75) Inventors: Olan S. Fruchey, Hurricane, WV (US); Leo E. Manzer, Wilmington, DE (US); Dilum Dunuwila, Princeton, NJ (US); Brian T. Keen, Pinch, WV (US); Brooke A. Albin, Charleston, WV (US); Nye A. Clinton, Hurricane, WV (US); Bernard D. Dombek, Charleston, WV (US)

(73) Assignee: BioAmber Inc., Plymouth, MN (US)

( * ) Notice: Subject to any disclaimer, the term of this patent is extended or adjusted under 35 U.S.C. 154(b) by 0 days.

(21) Appl. No.: 13/701,570

(22) PCT Filed: Jun. 10, 2011

(86) PCT No.: PCT/US2011/039903
§ 371 (c)(1),
(2), (4) Date: Jan. 8, 2013

(87) PCT Pub. No.: WO2011/159557
PCT Pub. Date: Dec. 22, 2011

(65) Prior Publication Data
US 2013/0324694 A1    Dec. 5, 2013

Related U.S. Application Data

(60) Provisional application No. 61/355,205, filed on Jun. 16, 2010.

(51) Int. Cl.
*C08G 63/02* (2006.01)
*C08G 64/00* (2006.01)

(52) U.S. Cl.
USPC .......................................... 528/323

(58) Field of Classification Search
USPC .......................................... 528/323
See application file for complete search history.

(56) References Cited

U.S. PATENT DOCUMENTS

| | | |
|---|---|---|
| 2,223,303 A | 11/1940 | Lazier et al. |
| 3,296,303 A | 1/1967 | Nemec et al. |
| 3,579,583 A | 5/1971 | Rutzen |
| 4,003,933 A | 1/1977 | Drake |
| 4,237,067 A | 12/1980 | Küster et al. |
| 4,935,546 A | 6/1990 | Barrault et al. |
| 5,109,104 A | 4/1992 | Marks |
| 5,151,543 A | 9/1992 | Ziemecki |
| 5,487,987 A | 1/1996 | Frost et al. |
| 5,587,498 A | 12/1996 | Krogh et al. |
| 5,616,496 A | 4/1997 | Frost et al. |
| 6,057,442 A | 5/2000 | Wulff-Doring et al. |
| 6,376,714 B1 | 4/2002 | Allgeier et al. |
| 6,958,381 B2 | 10/2005 | Winterling et al. |
| 7,132,562 B2 | 11/2006 | Allgeier |
| 2009/0305364 A1 | 12/2009 | Burgard et al. |

FOREIGN PATENT DOCUMENTS

| | | |
|---|---|---|
| DE | 27 18 363 | 10/1978 |
| WO | 2010/003728 A1 | 1/2010 |
| WO | 2010/063632 A1 | 6/2010 |

OTHER PUBLICATIONS

Draths, K.M. et al., "Environmentally Compatible Synthesis of Adipic Acid from D-Glucose," *J. Am. Chem. Soc.*, 1994, vol. 116, pages 399-400 (p. 399 only).
Niu, W. et al., "Benzene-Free Synthesis of Adipic Acid," *Biotechnology Progress*, 2002, vol. 18, pp. 201-211 (Abstract only).
J. E. Carnahan et al., "Ruthenium-Catalyzed Hydrogenation of Acids to Alcohols, *Contribution No. 359 From the Chemical Department and Polychemicals Department, Experimental Station, E.I. Du Pont De Nemours & Co., Inc.*", Jan. 7, 1955, vol., 77, pp. 3766-2768.

*Primary Examiner* — Terressa Boykin
(74) *Attorney, Agent, or Firm* — DLA Piper LLP (US)

(57) ABSTRACT

Processes for producing nitrogen containing compounds include producing hexamethylenediamine (HMD), adiponitrile (ADN), adipamide (ADM) and derivatives thereof from adipic acid (AA) obtained from fermentation broths containing diammonium adipate (DAA) or monoammonium adipate (MAA).

18 Claims, 3 Drawing Sheets

SEQUENCE LISTING

<160> NUMBER OF SEQ ID NOS: 2

<210> SEQ ID NO 1
<211> LENGTH: 1644
<212> TYPE: DNA
<213> ORGANISM: Acinetobacter sp.

<400> SEQUENCE: 1

```
atggagatta tcatgtcaca aaaaatggat tttgatgcta tcgtgattgg tggtggtttt     60
ggcggacttt atgcagtcaa aaaattaaga gacgagctcg aacttaaggt tcaggctttt    120
gataaagcca cggatgtcgc aggtacttgg tactggaacc gttacccagg tgcattgtcg    180
gatacagaaa cccacctcta ctgctattct tgggataaag aattactaca atcgctagaa    240
atcaagaaaa aatatgtgca aggccctgat gtacgcaagt atttacagca agtggctgaa    300
aagcatgatt taagaagag ctatcaattc aataccgcgg ttcaatcggc tcattacaac    360
gaagcagatg ccttgtggga agtcaccact gaatatggtg ataagtacac ggcgcgtttc    420
ctcatcactg ctttaggctt attgtctgcg cctaacttgc aaacatcaa aggcattaat    480
cagtttaaag gtgagctgca tcataccagc cgctggccag atgacgtaag ttttgaaggt    540
aaacgtgtcg gcgtgattgg tacgggttcc accggtgttc aggttattac ggctgtggca    600
cctctggcta acacctcac tgtcttccag cgttctgcac aatacagcgt tccaattggc    660
aatgatccac tgtctgaaga agatgttaaa aagatcaaag acaattatga caaaatttgg    720
gatggtgtat ggaattcagc ccttgccttt ggcctgaatg aaagcacagt gccagcaatg    780
agcgtatcag ctgaagaacg caaggcagtt tttgaaaagg catggcaaac aggtggcggt    840
ttccgtttca tgtttgaaac tttcggtgat attgccacca atatggaagc caatatcgaa    900
gcgcaaaatt tcattaaggg taaaattgct gaaatcgtca agatccagc cattgcacag    960
aagcttatgc cacaggattt gtatgcaaaa cgtccgttgt gtgacagtgg ttactacaac   1020
acctttaacc gtgacaatgt ccgtttagaa gatgtgaaag ccaatccgat tgttgaaatt   1080
accgaaaacg tgtgaaact cgaaaatggc gatttcgttg aattagacat gctgatatgt   1140
gccacaggtt ttgatgccgt cgatggcaac tatgtgcgca tggacattca aggtaaaaac   1200
ggcttggcca tgaaagacta ctggaaagaa ggtccgtcga gctatatggg tgtcaccgta   1260
aataactatc aaacatgtt catggtgctt ggaccgaatg gccgtttac caacctgccg   1320
ccatcaattg aatcacaggt ggaatggatc agtgatacca ttcaatacac ggttgaaaac   1380
aatgttgaat ccattgaagc gacaaaagaa gcggaagaac aatggactca aacttgcgcc   1440
aatattgcgg aaatgacctt attccctaaa gcgcaatcct ggattttttgg tgcgaatatc   1500
ccgggcaaga aaaacacggt ttacttctat ctcggtggtt aaaagaata tcgcagtgcg   1560
ctagccaact gcaaaaacca tgcctatgaa ggttttgata ttcaattaca acgttcagat   1620
atcaagcaac tgccaatgc ctaa                                          1644
```

<210> SEQ ID NO 2
<211> LENGTH: 547
<212> TYPE: PRT
<213> ORGANISM: Acinetobacter sp.

<400> SEQUENCE: 2

```
Met Glu Ile Ile Met Ser Gln Lys Met Asp Phe Asp Ala Ile Val Ile
1               5                   10                  15

Gly Gly Gly Phe Gly Gly Leu Tyr Ala Val Lys Lys Leu Arg Asp Glu
            20                  25                  30

Leu Glu Leu Lys Val Gln Ala Phe Asp Lys Ala Thr Asp Val Ala Gly
        35                  40                  45

Thr Trp Tyr Trp Asn Arg Tyr Pro Gly Ala Leu Ser Asp Thr Glu Thr
    50                  55                  60

His Leu Tyr Cys Tyr Ser Trp Asp Lys Glu Leu Leu Gln Ser Leu Glu
65                  70                  75                  80
```

-continued

```
Ile Lys Lys Lys Tyr Val Gln Gly Pro Asp Val Arg Lys Tyr Leu Gln
            85                  90                  95

Gln Val Ala Glu Lys His Asp Leu Lys Lys Ser Tyr Gln Phe Asn Thr
            100                 105                 110

Ala Val Gln Ser Ala His Tyr Asn Glu Ala Asp Ala Leu Trp Glu Val
            115                 120                 125

Thr Thr Glu Tyr Gly Asp Lys Tyr Thr Ala Arg Phe Leu Ile Thr Ala
            130                 135                 140

Leu Gly Leu Leu Ser Ala Pro Asn Leu Pro Asn Ile Lys Gly Ile Asn
145                 150                 155                 160

Gln Phe Lys Gly Glu Leu His His Thr Ser Arg Trp Pro Asp Asp Val
            165                 170                 175

Ser Phe Glu Gly Lys Arg Val Gly Val Ile Gly Thr Gly Ser Thr Gly
            180                 185                 190

Val Gln Val Ile Thr Ala Val Ala Pro Leu Ala Lys His Leu Thr Val
            195                 200                 205

Phe Gln Arg Ser Ala Gln Tyr Ser Val Pro Ile Gly Asn Asp Pro Leu
            210                 215                 220

Ser Glu Glu Asp Val Lys Lys Ile Lys Asp Asn Tyr Asp Lys Ile Trp
225                 230                 235                 240

Asp Gly Val Trp Asn Ser Ala Leu Ala Phe Gly Leu Asn Glu Ser Thr
            245                 250                 255

Val Pro Ala Met Ser Val Ser Ala Glu Glu Arg Lys Ala Val Phe Glu
            260                 265                 270

Lys Ala Trp Gln Thr Gly Gly Phe Arg Phe Met Phe Glu Thr Phe
            275                 280                 285

Gly Asp Ile Ala Thr Asn Met Glu Ala Asn Ile Glu Ala Gln Asn Phe
            290                 295                 300

Ile Lys Gly Lys Ile Ala Glu Ile Val Lys Asp Pro Ala Ile Ala Gln
305                 310                 315                 320

Lys Leu Met Pro Gln Asp Leu Tyr Ala Lys Arg Pro Leu Cys Asp Ser
            325                 330                 335

Gly Tyr Tyr Asn Thr Phe Asn Arg Asp Asn Val Arg Leu Glu Asp Val
            340                 345                 350

Lys Ala Asn Pro Ile Val Glu Ile Thr Glu Asn Gly Val Lys Leu Glu
            355                 360                 365

Asn Gly Asp Phe Val Glu Leu Asp Met Leu Ile Cys Ala Thr Gly Phe
            370                 375                 380

Asp Ala Val Asp Gly Asn Tyr Val Arg Met Asp Ile Gln Gly Lys Asn
385                 390                 395                 400

Gly Leu Ala Met Lys Asp Tyr Trp Lys Glu Gly Pro Ser Ser Tyr Met
            405                 410                 415

Gly Val Thr Val Asn Asn Tyr Pro Asn Met Phe Met Val Leu Gly Pro
            420                 425                 430

Asn Gly Pro Phe Thr Asn Leu Pro Pro Ser Ile Glu Ser Gln Val Glu
            435                 440                 445

Trp Ile Ser Asp Thr Ile Gln Tyr Thr Val Asn Asn Val Glu Ser
            450                 455                 460

Ile Glu Ala Thr Lys Glu Ala Glu Glu Gln Trp Thr Gln Thr Cys Ala
465                 470                 475                 480

Asn Ile Ala Glu Met Thr Leu Phe Pro Lys Ala Gln Ser Trp Ile Phe
            485                 490                 495

Gly Ala Asn Ile Pro Gly Lys Lys Asn Thr Val Tyr Phe Tyr Leu Gly
            500                 505                 510
```

```
Gly Leu Lys Glu Tyr Arg Ser Ala Leu Ala Asn Cys Lys Asn His Ala
        515                 520                 525

Tyr Glu Gly Phe Asp Ile Gln Leu Gln Arg Ser Asp Ile Lys Gln Pro
        530                 535                 540

Ala Asn Ala
545
```

PROCESSES FOR PRODUCING HEXAMETHYLENEDIAMINE (HMD), ADIPONITRILE (ADN), ADIPAMIDE (ADM) AND DERIVATIVES THEREOF

RELATED APPLICATION

This is a §371 of International Application No. PCT/US2011/039903, with an international filing date of Jun. 10, 2011 (WO 2011/159557 A1, published Dec. 22, 2011), which is based on U.S. patent application Ser. No. 61/355,205 filed Jun. 16, 2010, the subject matter of which is incorporated herein by reference.

This disclosure contains a Sequence Listing which has been submitted in ASCII format via EFS-Web and is hereby incorporated by reference in its entirely. Said ASCII copy, created on Jan. 16, 2013, is named DN1209US.txt and is 7,517 bytes in size.

TECHNICAL FIELD

This disclosure relates to processes for producing hexamethylenediamine (HMD), adiponitrile (ADN), adipamide (ADM) and derivatives thereof from adipic acid (AA) obtained from fermentation broths containing diammonium adipate (DAA) or monoammonium adipate (MAA).

BACKGROUND

Certain carbonaceous products of sugar fermentation are seen as replacements for petroleum-derived materials for use as feedstocks for the manufacture of carbon-containing chemicals. One such product is AA. Given such a process for the direct production of substantially pure AA from a DAA-containing fermentation broth or MAA-containing fermentation broth and the possible use of such AA as a source material for the production of HMD, ADN and ADM, it could be helpful to provide process for producing HMD, ADN and ADM and derivatives thereof in an economic and environmentally friendly way.

SUMMARY

We provide a process for producing nitrogen containing components including providing a clarified DAA-containing or MAA-containing fermentation broth; distilling the broth under super atmospheric pressure at a temperature of greater than 100° C. to about 300° C. to form an overhead that includes water and ammonia, and a liquid bottoms that includes AA, and at least about 20 wt % water; cooling the liquid bottoms to a temperature sufficient to cause the liquid bottoms to separate into a liquid portion and a solid portion that is substantially pure AA; separating the solid portion from the liquid portion; recovering the solid portion; (1) contacting at least a part of the solid portion with hydrogen and an ammonia source in the presence of at least one hydrogenation catalyst to produce HMD, (2) dehydrating at least a part of the solid portion in the presence of an ammonia source to produce ADN or (3) separating the solid portion from the liquid portion; and dehydrating at least a part of the solid portion in the presence of an ammonia source to produce ADM; and recovering the HMD, ADN or ADM.

We also provide a process for producing nitrogen containing compounds including providing a clarified DAA-containing or MAA-containing fermentation broth; adding an ammonia separating solvent to the broth; distilling the broth at a temperature and pressure sufficient to form an overhead that includes water and ammonia, and a liquid bottoms that includes AA, and at least about 20 wt % water; cooling the bottoms to a temperature sufficient to cause the bottoms to separate into a liquid portion and a solid portion that is substantially pure AA; separating the solid portion from the liquid portion; recovering the solid portion; (1) contacting at least a part of the solid portion with hydrogen and an ammonia source in the presence of at least one hydrogenation catalyst to produce HMD, (2) dehydrating at least a part of the solid portion in the presence of an ammonia source to produce ADN or (3) separating the solid portion from the liquid portion; and dehydrating at least a part of the solid portion in the presence of an ammonia source to produce ADM; and recovering the HMD, ADN or ADM.

DETAILED DESCRIPTION

It will be appreciated that at least a portion of the following description is intended to refer to representative examples of processes selected for illustration in the drawings and is not intended to define or limit the disclosure, other than in the appended claims.

Figure 1:
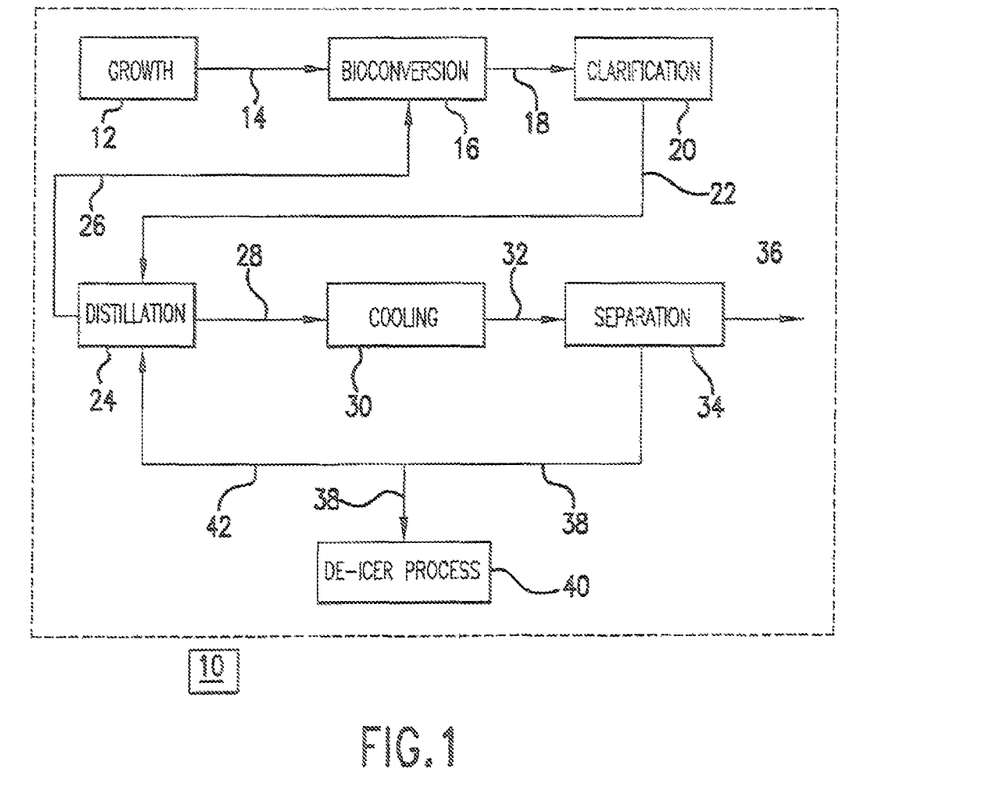
FIG. 1 is a block diagram of a process for making AA from a DAA containing broth.

Our processes may be appreciated by reference to FIG. 1, which shows in block diagram form one representative example of a bioprocessing system 10.

A growth vessel 12, typically an in-place steam sterilizable fermentor, may be used to grow a microbial culture (not shown) that is subsequently utilized for producing the DAA, MAA and/or AA-containing fermentation broth. Such growth vessels are known in the art and are not further discussed.

The microbial culture may comprise microorganisms capable of producing adipic acid from fermentable carbon sources such as carbohydrate sugars. Representative examples of microorganisms include *Escherichia coli* (*E. coli*), *Aspergillus niger*, *Corynebacterium glutamicum* (also called *Brevibacteriumflavum*), *Enterococcus faecalis*, *Veillonella parvula*, *Actinobacillus succinogenes*, *Paecilomyces varioti*, *Saccharomyces cerevisiae*, *Candida tropicalis*, *Bacteroides fragilis*, *Bacteroides ruminicola*, *Bacteroides amylophilus*, *Lebsiella pneumonae* mixtures thereof and the like.

Preferred microorganisms include the *Candida tropicalis* (Castellani) Berkhout, anamorph strain OH23 having ATCC accession number 24887, *E. coli* strain AB2834/pKD136/pKD8.243A/pKD8.292 having ATCC accession number 69875, the *E. coli* cosmid clones designated 5B12, 5F5, 8F6 and 14D7 comprising a vector expressing the cyclohexanone monooxygenase having the amino acid sequence shown in SEQ ID NO: 2 and encoded by SEQ ID NO: 1 from *Acinetobacter* strain SE19, and the yeast strain available from verdezyne, Inc. (Carslbad, Calif., USA; hereinafter "Verdezyne Yeast") which produces AA from alkanes and other carbon sources.

Fermentation broths containing AA can be produced from the *Candida tropicalis* (Castellani) Berkhout, anamorph strain OH23 having ATCC accession number 24887 by culture at 32° C. in a liquid medium containing 300 mg of NH₄H₂PO₄, 200 mg of KH₂PO₄, 100 mg of K₂HPO₄, 50 mg of MgSO₄.7H₂O, 1 µg of biotin, 0.1% (w/v) yeast extract and about 1% (v/v) n-hexadecane in 100 ml of distilled water. Other culture media such as YM broth containing n-hexadecane may also be used. The procedure for producing fermentation broths containing AA from media containing n-hexadecane by culturing *Candida tropicalis* (Castellani) Berkhout, anamorph strain OH23 having ATCC accession number 24887 is also described in Okuhura et al., 35 Agr. Biol. Chem. 1376 (1971) the subject matter of which is incorporated herein by reference.

Fermentation broths containing AA can also be produced from *E. coli* strain AB2834/pKD136/pKD8.243A/pKD8.292 having ATCC accession number 69875. This can be done as follows. One liter of LB medium (in 4 L Erlenmeyer shake flask) containing IPTG (0.2 mM), ampicillin (0.05 g), chloramphenicol (0.02 g) and spectinomycin (0.05 g) can be inoculated with 10 mL of an overnight culture of *E. coli* strain AB2834/pKD136/pKD8.243A/pKD8.292 cells grown at 250 rpm for 10 h at 37° C. The cells can be harvested, resuspended in 1 L of M9 minimal medium containing 56 mM D-glucose, shikimic acid (0.04 g), IPTG (0.2 mM), ampicillin (0.05 g), chloramphenicol (0.02 g) and spectinomycin (0.05 g). The cultures can then be returned to 37° C. incubation. After resuspension in minimal medium the pH of the culture can be closely monitored, particularly over the initial 12 h. When the culture reaches a pH of 6.5, 5N NaOH or an appropriate amount of another base such as ammonium hydroxide can be added to adjust the pH back to approximately 6.8. Over the 48 h accumulation period, the culture should not allowed to fall below pH 6.3. After 24 h in the medium 12 mM cis, cis-muconate and 1 mM protocatechuate may be detected in the culture supernatant along with 23 mM D-glucose. After 48 h in the medium *E. coli* strain AB2834/pKD136/pKD8.243A/pKD8.292 cells can essentially replace the 56 mM D-glucose in the medium with 17 mM cis, cis-muconate.

The reduction of microbially synthesized cis, cis-muconate AA to produce a fermentation broth containing AA can then proceed as follows. Fifty milligrams of platinum on carbon (10%) can be added to 6 mL of a cell-free culture supernatant from the fermentation containing about 17.2 mM cis, cis-muconate. This sample can then be hydrogenated at 50 psi hydrogen pressure for 3 h at room temperature to produce a fermentation broth containing AA. The fermentation broth produced in this fashion may contain, for example, about 15.1 mM AA. The procedure for producing fermentation broths containing AA by culturing *E. coli* strain AB2834/pKD136/pKD8.243A/pKD8.292 cells by culture in a growth medium comprising D-glucose is also described in Draths & Frost, 116 J. Am. Chem. Soc. 399 (1994); Draths and Frost, 18 Biotechnol. Prog. 201 (2002); U.S. Pat. Nos. 5,487,987 and 5,616,496 the subject matter of which is incorporated herein by reference.

Fermentation broths containing AA can also be produced from the *E. coli* cosmid clones designated 5B12, 5F5, 8F6 and 14D7 comprising a vector expressing the cyclohexanone monooxygenase SEQ ID NO: 2 encoded by SEQ ID NO: 1 from *Acinetobacter* strain SE19 by culturing these clones in M9 minimal medium supplemented with 0.4% glucose as the carbon source. Cells can be grown at 30° C. with shaking for 2 h and the addition of 330 ppm of cyclohexanol to the medium. This can be followed by further incubation at 30° C. for an additional period of time such as, for example, 2 h, 4 h or 20 h or other time intervals. The procedure for producing fermentation broths containing AA by culturing the *E. coli* cosmid clones designated 5B12, 5F5, 8F6 and 14D7 comprising a vector expressing the cyclohexanone monooxygenase encoded by SEQ ID NO: 1 from *Acinetobacter* strain SE19 in a growth medium comprising D-glucose and clyclohexanol is also described in U.S. Pat. No. 6,794,165 the subject matter of which is incorporated herein by reference.

Fermentation broths containing AA can also be produced with the Verdezyne Yeast strain available from Verdezyne, Inc. (Carslbad, Calif., USA) which was reported on Feb. 8, 2010 to produce AA when cultured in a medium (e.g., SD medium) comprising alkanes or other carbon sources such as sugars and plant-based oils.

Fermentation broths containing AA can also be produced from *E. coli* or other microorganisms transformed with nucleic acids encoding succinyl-CoA:acetyl-CoA acyl transferase; 3-hydroxyacyl-CoA dehydrogenase; 3-hydroxyadipyl-CoA dehydratase; 5-carboxy-2-pentenoyl-CoA reductase; adipyl-CoA synthetase, phosphotransadipylase/adipate kinase, adipyl-CoA transferase or adipyl-CoA hydrolase. Fermentation broths containing AA can also be produced from *E. coli* or other microorganisms transformed with nucleic acids encoding succinyl-CoA:acetyl-CoA acyl transferase; 3-oxoadipyl-CoA transferase; 3-oxoadipate reductase; 3-hydroxyadipate dehydratase; and 2-enoate reductase. Fermentation broths containing AA can also be produced from *E. coli* or other microorganisms transformed with nucleic acids encoding alpha-ketoadipyl-CoA synthetase, phosphotransketoadipylase/alpha-ketoadipate kinase or alpha-ketoadipyl-CoA:acetyl-CoA tranferase; 2-hydroxyadipyl-CoA dehydrogenase; 2-hydroxyadipyl-CoA dehydratase; 5-carboxy-2-penteoyl-CoA reductase; and adipyl-CoA synthetase, phosphotransadipylase/adipate kinase, adipyl-CoA:acetyl-CoA transferase or adipyl-CoA hydrolase. Fermentation broths containing AA can also be produced from *E. coli* or other microorganisms transformed with nucleic acids encoding 2-hydroxyadipate dehydrogenase; 2-hydroxyadipyl-CoA synthetase, phosphotranshydroxyadipylase/2-hydroxy-adipate kinase or 2-hydroxyadipyl-CoA:acetyl-CoA transferase; 2-hydroxyadipyl-CoA dehydratase; 5-carboxy-2-pentenoyl-CoA reductase; and adipyl-CoA synthetase, phosphotrans-adipylase/adipate kinase, adipyl-CoA:acetyl-CoA transferase or adipyl-CoA hydrolase. Fermentations with *E. coli* or other microorganisms transformed with nucleic acids encoding these enzymes may be performed using a variety of different carbon sources under standard conditions in standard culture mediums (e.g., M9 minimal medium) and appropriate antibiotic or nutritional supplements necessary to maintain the transformed phenotype. The procedure for producing fermentation broths containing AA by culturing *E. coli* or other microorganisms transformed with nucleic acids encoding these enzymes, appropriate growth mediums and carbon sources are also described in US 2009/0305364, the subject matter of which is incorporated herein by reference.

Procedures for producing fermentation broths containing dicarboxylic acids such as AA by culturing *Saccharomyces cerevisiae* and other strains, microorganism strains, appropriate growth mediums and carbon sources are also described in WO 2010/003728, the subject matter of which is incorporated herein by reference.

A fermentable carbon source (e.g., carbohydrates and sugars), optionally a source of nitrogen and complex nutrients (e.g., corn steep liquor), additional media components such as vitamins, salts and other materials that can improve cellular growth and/or product formation, and water may be fed to the growth vessel 12 for growth and sustenance of the microbial culture. Typically, the microbial culture is grown under aerobic conditions provided by sparging an oxygen-rich gas (e.g., air or the like). Typically, an acid (e.g., sulphuric acid or the like) and ammonium hydroxide are provided for pH control during the growth of the microbial culture.

In one example (not shown), the aerobic conditions in growth vessel 12 (provided by sparging an oxygen-rich gas) are switched to anaerobic conditions by changing the oxygen-rich gas to an oxygen-deficient gas (e.g., $CO_2$ or the like). The anaerobic environment may trigger bioconversion of the fermentable carbon source to AA in situ in growth vessel 12. Ammonium hydroxide is provided for pH control during bioconversion of the fermentable carbon source to AA. The AA that is produced is at least partially if not totally neutralized to DAA due to the presence of the ammonium hydroxide, leading to the production of a broth comprising DAA. $CO_2$ may be an additional source of carbon for the production of AA.

In another example, the contents of growth vessel 12 may be transferred via stream 14 to a separate bioconversion vessel 16 for bioconversion of a carbohydrate source to AA. An oxygen-deficient gas (e.g., $CO_2$ or the like) is sparged in bioconversion vessel 16 to provide anaerobic conditions that trigger production of AA. Ammonium hydroxide is provided for pH control during bioconversion of the carbohydrate source to AA. Due to the presence of the ammonium hydroxide, the AA produced is at least partially neutralized to DAA, leading to production of a broth that comprises DAA. $CO_2$ may be an additional source of carbon for production of AA.

In yet another example, the bioconversion may be conducted at relatively low pH (e.g., about 3 to about 6). A base (ammonium hydroxide or ammonia) may be provided for pH control during bioconversion of the carbohydrate source to AA. Depending on the desired pH, due to the presence or lack of the ammonium hydroxide, either AA is produced or the AA produced is at least partially neutralized to MAA, DAA or a mixture comprising AA, MAA and/or DAA. Thus, the AA produced during bioconversion can be subsequently neutralized, optionally in an additional step, by providing either ammonia or ammonium hydroxide leading to a broth comprising DAA. As a consequence, a "DAA-containing fermentation broth" generally means that the fermentation broth comprises DAA and possibly any number of other components such as MAA and/or AA, whether added and/or produced by bioconversion or otherwise. Similarly, a "MAA-containing fermentation broth" generally means that the fermentation broth comprises MAA and possibly any number of other components such as DAA and/or AA, whether added and/or produced by bioconversion or otherwise.

The broth resulting from the bioconversion of the fermentable carbon source (in either growth vessel 12 or bioconversion vessel 16, depending on where the bioconversion takes place), typically contains insoluble solids such as cellular biomass and other suspended material, which are transferred via stream 18 to clarification apparatus 20 before distillation. Removal of insoluble solids clarifies the broth. This reduces or prevents fouling of subsequent distillation equipment. The insoluble solids can be removed by any one of several solid-liquid separation techniques, alone or in combination, including but not limited to, centrifugation and filtration (including, but not limited to ultra-filtration, micro-filtration or depth filtration). The choice of filtration can be made using techniques known in the art. Soluble inorganic compounds can be removed by any number of known methods such as, but not limited to, ion-exchange, physical adsorption and the like.

An example of centrifugation is a continuous disc stack centrifuge. It may be useful to add a polishing filtration step following centrifugation such as dead-end or cross-flow filtration, which may include the use of a filter aide such as diatomaceous earth or the like, or more preferably ultra-filtration or micro-filtration. The ultra-filtration or micro-filtration membrane can be ceramic or polymeric, for example. One example of a polymeric membrane is SelROMPS-U20P (pH stable ultra-filtration membrane) manufactured by Koch Membrane Systems (850 Main Street, Wilmington, Mass., USA). This is a commercially available polyethersulfone membrane with a 25,000 Dalton molecular weight cut-off which typically operates at pressures of about 0.35 to about 1.38 MPa (maximum pressure of about 1.55 MPa) and at temperatures up to about 50° C. Alternatively, a filtration step may be employed alone using ultra-filtration or micro-filtration.

The resulting clarified DAA-containing broth or MAA-containing broth, substantially free of the microbial culture and other solids, is transferred via stream 22 to distillation apparatus 24.

The clarified distillation broth should contain DAA in an amount that is at least a majority of, preferably at least about 70 wt %, more preferably about 80 wt % and most preferably at least about 90 wt % of all the diammonium dicarboxylate salts in the broth. The concentration of DAA and/or MAA as a weight percent (wt %) of the total dicarboxylic acid salts in the fermentation broth can be determined by high pressure liquid chromatography (HPLC) or other known means.

Water and ammonia are removed from distillation apparatus 24 as an overhead, and at least a portion may optionally be recycled via stream 26 to bioconversion vessel 16 (or growth vessel 12 operated in the anaerobic mode).

The specific distillation temperature and pressure are not critical as long as the distillation is carried out in a way that ensures that the distillation overhead contains water and ammonia, and the distillation bottoms comprises at least some AA and at least about 20 wt % water. A more preferred amount of water is at least about 30 wt % and an even more preferred amount is at least about 40 wt %. The rate of ammonia removal from the distillation step increases with increasing temperature and also can be increased by injecting steam (not shown) during distillation. The rate of ammonia removal during distillation may also be increased by conducting distillation under a vacuum or by sparging the distillation apparatus with a non-reactive gas such as air, nitrogen or the like.

Removal of water during the distillation step can be enhanced by the use of an organic azeotroping agent such as toluene, xylene, methylcyclohexane, methyl isobutyl ketone, cyclohexane, heptane or the like, provided that the bottoms contains at least about 20 wt % water. If the distillation is carried out in the presence of an organic agent capable of forming an azeotrope consisting of the water and the agent, distillation produces a biphasic bottoms that comprises an aqueous phase and an organic phase, in which case the aqueous phase can be separated from the organic phase, and the aqueous phase used as the distillation bottoms. By-products such as adipimide and adipamide are substantially avoided provided the water level in the bottoms is maintained at a level of at least about 30 wt %.

A preferred temperature for the distillation step is in the range of about 50° C. to about 300° C., depending on the pressure. A more preferred temperature range is about 150° C. to about 240° C., depending on the pressure. A distillation temperature of about 170° C. to about 230° C. is preferred. "Distillation temperature" refers to the temperature of the bottoms (for batch distillations this may be the temperature at the time when the last desired amount of overhead is taken).

Adding a water miscible organic solvent or an ammonia separating solvent may facilitate deammoniation over a variety of distillation temperatures and pressures as discussed above. Such solvents include aprotic, bipolar, oxygen-containing solvents that may be able to form passive hydrogen bonds. Examples include, but are not limited to, diglyme, triglyme, tetraglyme, sulfoxides such as dimethylsulfoxide (DMSO), amides such as dimethylformamide (DMF) and dimethylacetamide, sulfones such as dimethylsulfone, gamma-butyrolactone (GBL), sulfolane, polyethyleneglycol (PEG), butoxytriglycol, N-methylpyrolidone (NMP), ethers such as dioxane, methyl ethyl ketone (MEK) and the like. Such solvents can aid in the removal of ammonia from the DAA or MAA in the clarified broth. Regardless of the distillation technique, it is important that the distillation be carried out in a way that ensures that at least some MAA and at least about 20 wt % water remain in the bottoms and even more advantageously at least about 30 wt %. The distillation can be performed at atmospheric, sub-atmospheric or super-atmospheric pressures.

Under other conditions, such as when the distillation is conducted in the absence of an azeotropic agent or ammonia separating solvent, the distillation is conducted at super atmospheric pressure at a temperature of greater than 100° C. to about 300° C. to form an overhead that comprises water and ammonia and a liquid bottoms that comprises AA and at least about 20 wt % water. Super atmospheric pressure typically falls within a range of greater than ambient atmosphere up to and including about 25 atmospheres. Advantageously the amount of water is at least about 30 wt %.

The distillation can be a one-stage flash, a multistage distillation (i.e., a multistage column distillation) or the like. The one-stage flash can be conducted in any type of flasher (e.g., a wiped film evaporator, thin film evaporator, thermosiphon flasher, forced circulation flasher and the like). The multistages of the distillation column can be achieved by using trays, packing or the like. The packing can be random packing (e.g., Raschig rings, Pall rings, Berl saddles and the like) or structured packing (e.g., Koch-Sulzer packing, Intalox packing, Mellapak and the like). The trays can be of any design (e.g., sieve trays, valve trays, bubble-cap trays and the like). The distillation can be performed with any number of theoretical stages.

If the distillation apparatus is a column, the configuration is not particularly critical, and the column can be designed using well known criteria. The column can be operated in either stripping mode, rectifying mode or fractionation mode. Distillation can be conducted in either batch, semi-continuous or continuous mode. In the continuous mode, the broth is fed continuously into the distillation apparatus, and the overhead and bottoms are continuously removed from the apparatus as they are formed. The distillate from distillation is an ammonia/water solution, and the distillation bottoms is a liquid, aqueous solution of MAA and AA, which may also contain other fermentation by-product salts (i.e., ammonium acetate, ammonium formate, ammonium lactate and the like) and color bodies.

The distillation bottoms can be transferred via stream 28 to cooling apparatus 30 and cooled by conventional techniques. Cooling technique is not critical. A heat exchanger (preferably with heat recovery) can be used. A flash vaporization cooler can be used to cool the bottoms to about 15° C. Cooling to 15° C. typically employs a refrigerated coolant such as, for example, glycol solution or, less preferably, brine. A concentration step can be included prior to cooling to help increase product yield. Further, both concentration and cooling can be combined using known methods such as vacuum evaporation and heat removal using integrated cooling jackets and/or external heat exchangers.

Figure 2:
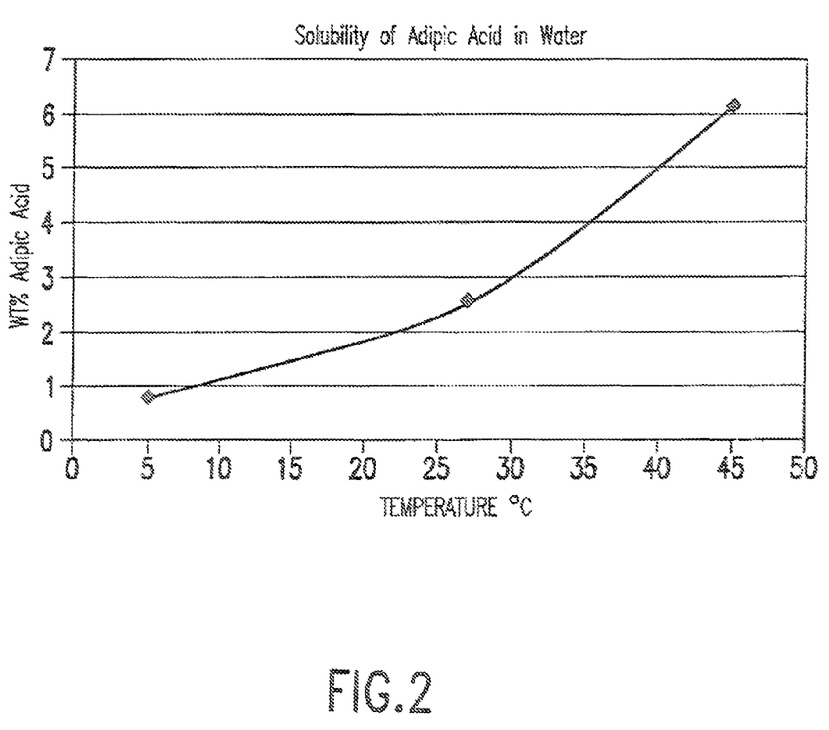
FIG. 2 is a graph showing the solubility of AA in water as a function of temperature.
Figure 3:
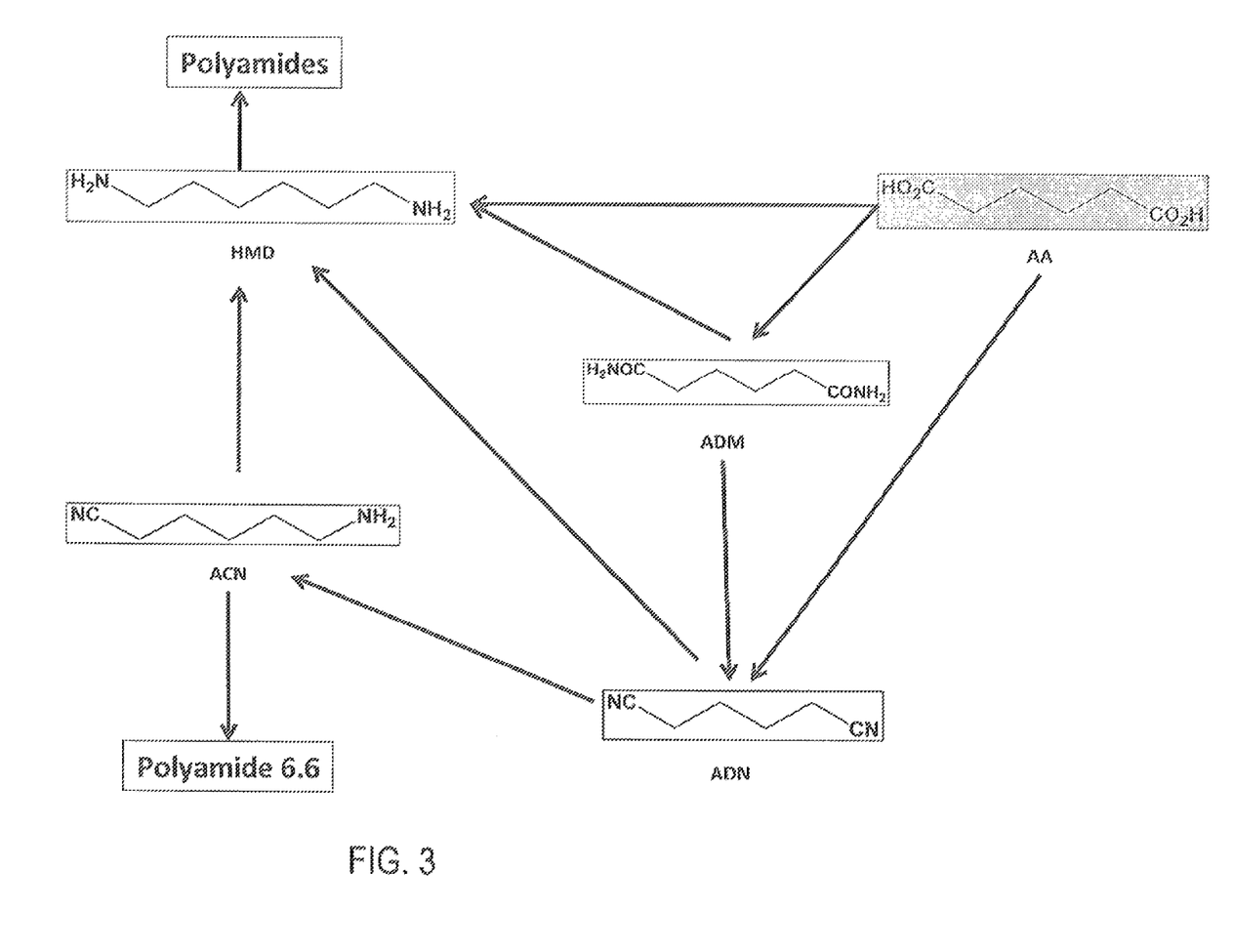
FIG. 3. is a flow diagram showing the selected production of HMD, ADN, ADM and derivatives thereof.

It has been found that the presence of some MAA in the liquid bottoms facilitates cooling-induced separation of the bottoms into a liquid portion in contact with a solid portion that at least "consists essentially" of AA (meaning that the solid portion is at least substantially pure crystalline AA) by reducing the solubility of AA in the liquid, aqueous, MAA-containing bottoms. FIG. 2 illustrates the solubility of AA in water. We discovered, therefore, that AA can be more completely crystallized out of an aqueous solution if some MAA is also present in that solution. A preferred concentration of MAA in such a solution is about 20 wt %. A more preferred concentration of MAA in such a solution is in the ppm to about 3 wt % range. This phenomenon allows crystallization of AA (i.e., formation of the solid portion of the distillation bottoms) at temperatures higher than those that would be required in the absence of MAA.

The distillation bottoms is fed via stream 32 to separator 34 for separation of the solid portion from the liquid portion. Separation can be accomplished via pressure filtration (e.g., using Nutsche or Rosenmond type pressure filters), centrifugation and the like. The resulting solid product can be recovered as product 36 and dried, if desired, by standard methods.

After separation, it may be desirable to treat the solid portion to ensure that no liquid portion remains on the surface(s) of the solid portion. One way to minimize the amount of liquid portion that remains on the surface of the solid portion is to wash the separated solid portion with water and dry the resulting washed solid portion. A convenient way to wash the solid portion is to use a so-called "basket centrifuge." Suitable basket centrifuges are available from The Western States Machine Company (Hamilton, Ohio, USA).

The liquid portion of the distillation bottoms 34 (i.e., the mother liquor) may contain remaining dissolved AA, any unconverted MAA, any fermentation by-products such as ammonium acetate, lactate, or formate, and other minor impurities. This liquid portion can be fed via stream 38 to a downstream apparatus 40. In one instance, apparatus 40 may be a means for making a de-icer by treating in the mixture with an appropriate amount of potassium hydroxide, for example, to convert the ammonium salts to potassium salts. Ammonia generated in this reaction can be recovered for reuse in the bioconversion vessel 16 (or growth vessel 12 operating in the anaerobic mode). The resulting mixture of potassium salts is valuable as a de-icer and anti-icer.

The mother liquor from the solids separation step 34, can be recycled (or partially recycled) to distillation apparatus 24 via stream 42 to further enhance recovery of AA, as well as further convert MAA to AA.

The solid portion of the cooling-induced crystallization is substantially pure AA and is, therefore, useful for the known utilities of AA. One such use is for the production of HMD, ADN, ADM and derivatives thereof.

HPLC can be used to detect the presence of nitrogen-containing impurities such as adipamide and adipimide. The purity of AA can be determined by elemental carbon and nitrogen analysis. An ammonia electrode can be used to determine a crude approximation of AA purity.

Depending on the circumstances and various operating inputs, there are instances when the fermentation broth may be a clarified MAA-containing fermentation broth or a clarified AA-containing fermentation broth. In those circumstances, it can be advantageous to add MAA, DAA and/or AA and, optionally, ammonia and/or ammonium hydroxide to those fermentation broths to facilitate the production of substantially pure AA. For example, the operating pH of the fermentation broth may be oriented such that the broth is a MAA-containing broth or a AA-containing broth. MAA, DAA, AA, ammonia and/or ammonium hydroxide may be added to those broths to attain a broth pH preferably less than 6 to facilitate production of the above-mentioned substantially pure AA. In one particular form, it is especially advantageous to recycle AA, MAA and water from the liquid bottoms resulting from the distillation step 24 into the fermentation broth and/or clarified fermentation broth. In referring to the MAA-containing broth, such broth generally means that the fermentation broth comprises MAA and possibly any number of other components such as DAA and/or AA, whether added and/or produced by bioconversion or otherwise.

The use of a synthetic DAA solution is believed to be a good model for the behavior of an actual broth in our processes because of the solubility of the typical fermentation by-products found in actual broth. The major by-products produced during fermentation are ammonium acetate, ammonium lactate and ammonium formate. Ammonium acetate, ammonium lactate and ammonium formate are significantly more soluble in water than AA, and each is typically present in the broth at less than 10% of the DAA concentration. In addition, even when the acids (acetic, formic and lactic acids) were formed during the distillation step, they are miscible with water and will not crystallize from water. This means that the AA reaches saturation and crystallizes from solution (i.e., forming the solid portion), leaving the acid impurities dissolved in the mother liquor (i.e., the liquid portion).

Streams comprising AA, MAA and/or DAA as described above may be converted to selected downstream products such as HMD, ADN, 6-aminocapronitrile (ACN), ADM and the like as described below. In initiating those processes, typically the AA, MAA and/or DAA may be dissolved in water to form an aqueous solution thereof which can be directly fed to the downstream reactor.

The AA, MAA or DAA may be converted to ADN, either directly or indirectly through the intermediate ADM by dehydration. Such dehydrations may be achieved thermally, enzymatically or in the presence of catalysts. Thus, appropriate temperatures, pressures and catalysts are selected to achieve the appropriate level of dehydration, depending on whether the conversion to ADN occurs directly or indirectly.

For example, the conversion may employ an appropriate dehydrating catalyst such as acidic or basic catalysts, including phosphates as disclosed in U.S. Pat. No. 4,237,067 and supported catalysts utilizing Ti, V, Hf or Zr on clays or alumina as disclosed in U.S. Pat. No. 5,587,498. Such catalysts are typically employed at temperatures of about 220° C. to about 350° C. at pressures of about 1.172 to 4.37 MPa, for example.

Alternatively, dehydration can be achieved thermally as disclosed in U.S. Pat. No. 3,296,303, wherein acids plus an ammonia source are thermally dehydrated in the presence of glycol solvents at temperatures of about 100° C. to 130° C. at pressures of about 1.03 to about 1.38 MPa.

As a consequence, AA, MAA or DAA may be dehydrated directly to ADN or indirectly to ADN by the intermediate ADM. Then, once ADN is produced, it is possible to convert ADN directly to an amine such as HMD or to indirectly convert ADN to HMD through the intermediate ACN.

For example, direct conversion from ADN to HMD can be achieved in any number of ways such as disclosed in U.S. Pat. No. 6,376,714 wherein dinitriles in the presence of hydrogen and an ammonia source are converted utilizing catalysts such as Fe, Co, Ni, Rh or Pd promoted with Ru, Cr or W at temperatures of about 50° C. to about 150° C. at about 2.01 to about 10.34 MPa. The result is high yields of the diamine, in this case HMD.

Similarly, U.S. Pat. No. 4,003,933 converts nitriles to amines with hydrogen over a Co/ZrO2 catalyst at about 120° C. to about 130° C. and at about 10.34 MPa. Other catalysts may include Fe, Rh, Ir and Pt on $TiO_2$ or $ZrO_2$.

The indirect conversion of ADN to ACN can be achieved by selecting appropriate hydrogenation conditions such as those disclosed in U.S. Pat. No. 5,151,543 wherein nitriles are converted to amino nitriles, in this case ADN to ACN, utilizing Raney catalysts such as Co or Ni promoted with Fe, Cr or Mo with hydrogen and an ammonia source at about 50° C. to about 80° C. at pressures of 1.72-6.89 MPa.

Similarly, the amino nitrile or diamino compounds can be co-produced from the dinitriles such as those disclosed in U.S. Pat. No. 7,132,562. US '562 utilizes Fe, Co, Ru, Ni catalysts modified with Cr, V, Ti or Mn at temperatures of about 50° C. to about 250° C. and 20.68 to 34.47 MPa to achieve high yields and selectivity to the diamine or amino nitrile. The catalysts may also be modified with ordinary P or N with HCN, or CO and hydrogen and an ammonia source.

It is also possible to convert AA, MAA or DAA directly to diamines such as HMD either directly or indirectly through ADM. For example, U.S. Pat. No. 2,223,303 discloses the conversion of acids to amines with hydrogen and an ammonia source or alkyl amines with a Cd or Cu catalyst at temperatures of about 200° C. to about 450° C. at pressures of about 1.01 to 30.4 MPa.

Similarly, U.S. Pat. No. 3,579,583 discloses the conversion of dicarboxylic acids to amines, particularly alkyl amines, utilizing hydrogen and an ammonia source at temperatures of 200° C. to 300° C. at pressures of 10.1 to 30.4 MPa in the presence of a Zn—$Al_2O_3$ or Zn—Cr catalyst.

Further, U.S. Pat. No. 4,935,546 discloses the conversion of acids to amines with hydrogen and an ammonia source in the presence of a Co, Cu or Cr catalyst on a $TiO_2$ or $Al_2O_3$ support at temperatures of 250° C. to 350° C. and at pressures of 2 to 15 MPa.

Once the conversions to HMD and ACN have been completed, it is also possible to convert those compounds into polyamide-type compounds in any number of ways known in the art. Representative examples include the following conversions. Polyamides may be produced from amino nitriles such as ACN. One example of conversions of this type may be found in U.S. Pat. No. 5,109,104 which converts an omega amino nitrile in the presence of an oxygenated phosphorus catalyst with water. This is generally achieved in a several-step conversion at temperatures of 200° C. to 330° C. and at pressures ranging from 1.72 to 2.41 MPa.

An alternative methodology is disclosed in U.S. Pat. No. 6,958,381 wherein a starting monomer such as ACN may be polymerized into the polyamide in the presence of a chain regulator containing a nitrile group and a functional group capable of forming a carboxamide group.

Polyamides may also be formed from the diamines such as HMD wherein the HMD is polymerized with a dicarboxylic acid or ester to form the polyamide. The preferred dicarboxylic acids have a chain length of $C_4$ to $C_{12}$. The dicarboxylic acid or ester may be an aromatic dicarboxylic acid or ester or it may be an alkyl dicarboxylic acid.

The subject matter and contents of the above-mentioned U.S. Pat. Nos. 4,237,067; 5,587,498; 3,296,303; 6,376,714; 4,003,933; 5,151,543; 7,132,562; 2,223,303; 3,579,583; 4,935,546; 5,109,104; and 6,958,381 are incorporated herein by reference.

Example 1

This example shows the conversion of DAA to MAA.

A 1-L round bottom flask was charged with 800 g of a synthetic 4.5% DAA solution. The flask was fitted with a five tray Oldershaw section which was capped with a distillation head. The distillate was collected in an ice cooled receiver. The contents of the flask were heated with a heating mantel and stirred with a magnetic stirrer. Distillation was started and 719.7 g of distillate collected. Titration of the distillate revealed it was a 0.29% ammonia solution (i.e. an about 61% conversion of DAA to MAA). The hot residue (76 g) was discharged from the flask and placed in an Erlenmeyer flask and slowly cooled to room temperature while stirring over a weekend. The contents were then cooled to 15° C. for 60 minutes and then cooled to 10° C. for 60 minutes and finally 5° C. for 60 minutes while stirring. The solids were filtered and dried in a vacuum oven for 2 hour at 75° yielding 16.2 g. Analysis of the solids for ammonia content by ammonia electrode indicated it was approximately a 1:1 molar ratio of ammonia and AA.

Example 2

This example shows the conversion of MAA to AA.

A 300 mL Parr autoclave was charged with 80 g of synthetic MAA and 124 g of water. The autoclave was sealed and the contents stirred and heated to about 200° C. (autogenic pressure was about 203 psig). Once the contents reached temperature, water was then fed to the autoclave at a rate of about 2 g/min and vapor was removed from the autoclave at a rate of about 2 g/min by means of a back pressure regulator. The vapor exiting the autoclave was condensed and collected in a receiver. The autoclave was run under these conditions until a total of 1210 g of water had been fed and a total of 1185 g of distillate collected. The contents of the autoclave (209 g) were partially cooled and discharged from the reactor. The slurry was allowed to stand stirring at room temperature over night in an Erlenmeyer flask. The slurry was then filtered and the solids rinsed with 25 g of water. The moist solids were dried in a vacuum oven at 75° C. for 1 hr yielding 59 g of AA product. Analysis via an ammonium ion electrode revealed 0.015 mmole ammonium ion/g of solid. The melting point of the recovered solid was 151 to 154° C.

Example 3

This example shows the conversion of DAA to MAA in the presence of a solvent.

A beaker was charged with 36.8 g of distilled water and 19.7 g of concentrated ammonium hydroxide. Then 23.5 g of adipic acid was slowly added. The mixture was stirred forming a clear solution which was then placed in a 500 mL round bottom flask which contained a stir bar. Triglyme (80 g) was then added to the flask. The flask was then fitted with a 5 tray 1" Oldershaw column section which was topped with a distillation head. The distillation head was fitted with an ice bath cooled receiver. The distillation flask was also fitted with an addition funnel which contained 150 g of distilled water. The contents were then stirred and heated with a heating mantel. When distillate began to come over the water in the addition funnel was added dropwise to the flask at the same rate as the distillate take-off. The distillation was stopped when all of the water in the addition funnel had been added. A total of 158 g of distillate had been collected. Titration of the distillate revealed a 1.6% ammonia content. This is equivalent to 46% of the charged ammonia. In other words the residue is a 91/9 mixture of monoammonium adipate/diammonium adipate. After cooling to room temperature, the residue was place in a 250 mL Erlenmeyer flask and slowly cooled to 5° C. while stirring. The slurry was filtered and the wet crystals were then dried in a vacuum oven for 2 hours yielding 5.5 g of solids. Analysis of the solids indicated essentially a one to one ratio of ammonium ion to adipate ion (i.e. monoammonium adipate).

Example 4

This example shows the conversion of MAA to AA in the presence of a solvent.

A beaker was charged with 46.7 g of distilled water and 9.9 g of concentrated ammonium hydroxide. Then 23.5 g of adipic acid was slowly added. The mixture was stirred forming a clear solution which was then placed in a 500 mL round bottom flask which contained a stir bar. Triglyme (80 g) was then added to the flask. The flask was then fitted with a 5 tray 1" Oldershaw column section which was topped with a distillation head. The distillation head was fitted with an ice bath cooled receiver. The distillation flask was also fitted with an addition funnel which contained 1800 g of distilled water. The contents were then stirred and heated with a heating mantel. When distillate began to come over the water in the addition funnel was added dropwise to the flask at the same rate as the distillate take-off. The distillation was stopped when all of the water in the addition funnel had been added. A total of 1806.2 g of distillate had been collected. Titration of the distillate revealed a 0.11% ammonia content. This is equivalent to 72% of the charged ammonia. In other words the residue is a 72/28 mixture of adipic acid/monoammonium adipate. The residue was then placed in an Erlenmeyer flask and cooled to 0° C. while stirring and allowed to stand for 1 hr. The slurry was filtered yielding 18.8 g of a wet cake and 114.3 g of mother liquor. The solids were then dried under vacuum at 80° C. for 2 hrs yielding 13.5 g of solids. The solids were then dissolved in 114 g of hot water and then cooled to 5° C. and held stirring for 45 minutes. The slurry was filtered yielding 13.5 g of wet solids and 109.2 g of mother liquor. The solids were dried under vacuum at 80° C. for 2 hrs yielding 11.7 g of dried solids. Analysis of the solids revealed an ammonium ion content of 0.0117 mmol/g (i.e. essentially pure adipic acid).

Although our processes have been described in connection with specific steps and forms thereof, it will be appreciated that a wide variety of equivalents may be substituted for the specified elements and steps described herein without departing from the spirit and scope of this disclosure as described in the appended claims.

The invention claimed is:

1. A process for producing nitrogen containing components comprising:
   (a) providing a clarified DAA-containing or MAA-containing fermentation broth;
   (b) distilling the broth under super atmospheric pressure at a temperature of greater than 100° C. to about 300° C. to form an overhead that comprises water and ammonia, and a liquid bottoms that comprises AA, and at least about 20 wt % water;
   (c) cooling and/or evaporating the liquid bottoms to a temperature and composition sufficient to cause the liquid bottoms to separate into a liquid portion and a solid portion that is substantially pure AA;
   (d) separating the solid portion from the liquid portion;
   (e) recovering the solid portion;
   (f) (1) contacting at least a part of the solid portion with hydrogen and an ammonia source in the presence of at least one hydrogenation catalyst to produce HMD, (2) dehydrating at least a part of the solid portion in the presence of an ammonia source to produce ADN or (3) separating the solid portion from the liquid portion; and dehydrating at least a part of the solid portion in the preselux of an ammonia source to produce ADM; and
   (g) recovering the HMD, ADN or ADM.

2. A process for producing nitrogen containing compounds comprising:
   (a) providing a clarified DAA-containing or MAA-containing fermentation broth;
   (b) adding an ammonia separating solvent to the broth;
   (c) distilling the broth at a temperature and pressure sufficient to form an overhead that comprises water and ammonia, and a liquid bottoms that comprises AA, and at least about 20 wt % water;
   (d) cooling the bottoms to a temperature sufficient to cause the bottoms to separate into a liquid portion and a solid portion that is substantially pure AA;
   (e) separating the solid portion from the liquid portion;
   (f) recovering the solid portion;
   (g) (1) contacting at least a part of the solid portion with hydrogen and an ammonia source in the presence of at least one hydrogenation catalyst to produce HMD, (2) dehydrating at least a part of the solid portion in the presence of an ammonia source to produce ADN or (3) separating the solid portion from the liquid portion; and dehydrating at least a part of the solid portion in the presence of an ammonia source to produce ADM; and
   (h) recovering the HMD, ADN or ADM.

3. The process of claim 2, wherein distilling the broth is carried out in the presence of an ammonia separating solvent which is at least one selected from the group consisting of diglyme, triglyme, tetraglyme, sulfoxides, amides, sulfones, polyethyleneglycol (PEG), butoxytriglycol, N-methylpyrolidone (NMP), ethers, and methyl ethyl ketone (MEK) or in the presence of a water azeotroping solvent which is at least one selected from the group consisting of toluene, xylene, methylcyclohexane, methyl isobutyl ketone, hexane, cyclohexane and heptane.

4. The process of claim 1, wherein dehydrating AA is conducted thermally, catalytically or enzymatically.

5. The processes of claim 1, further comprising polymerizing the HMD with a dicarboxylic acid or ester to form a polyamide.

6. The processes of claim 1, further comprising contacting the ADN with hydrogen and ammonia in the presence of a hydrogenation catalyst to produce HMD.

7. The process of claim 6, further comprising polymerizing the HMD with a dicarboxylic acid or ester to form a polyamide.

8. The processes of claim 1, further comprising contacting the ADN with hydrogen and ammonia in the presence of a hydrogenation catalyst to produce a composition comprising ACN.

9. The process of claim 8, further comprising polymerizing the ACN to form a polyamide.

10. The process of claim 8, further comprising contacting the ACN with hydrogen and ammonia in the presence of a hydrogenation catalyst to produce HMD.

11. The process of claim 10, further comprising polymerizing the HMD with a dicarboxylic acid or ester to form a polyamide.

12. The processes of claim 1, further comprising dehydrating the ADM to produce ADN.

13. The process of claim 12, further comprising contacting the ADN with hydrogen and ammonia in the presence of a hydrogenation catalyst to produce HMD.

14. The process of claim 13, further comprising polymerizing the HMD with a dicarboxylic acid or ester to form as polyamide.

15. The process of claim 12, further comprising contacting the ADN with hydrogen and ammonia in the presence of a hydrogenation catalyst to produce a composition comprising ACN.

16. The process of claim 15, further comprising polymerizing the ACN to form a polyamide.

17. The process of claim 15, further comprising contacting the ACN with hydrogen and ammonia in the presence of a hydrogenation catalyst to produce HMD.

18. The process of claim 17, further comprising polymerizing the HMD with a dicarboxylic acid or ester to form a polyamide.

* * * * *